United States Patent [19]

Lahitte et al.

[11] Patent Number: 5,077,522
[45] Date of Patent: Dec. 31, 1991

[54] DEVICE FOR THE DIELECTRIC CHARACTERIZATION OF SAMPLES MADE OF A MATERIAL HAVING A FLAT OR UNEVEN SURFACE AND APPLICATION FOR THE NON-DESTRUCTIVE CONTROL OF THE DIELECTRIC HOMOGENEITY OF SAID SAMPLES

[75] Inventors: Pierre Lahitte, Salaunes; Serge Villers, Le Bouscat, both of France

[73] Assignee: Aerospatiale Societe Nationale Industrielle, France

[21] Appl. No.: 577,763

[22] Filed: Sep. 5, 1990

[30] Foreign Application Priority Data

Sep. 5, 1989 [FR] France .................. 89 11582

[51] Int. Cl.⁵ .................. G01R 1/06; G01R 31/02
[52] U.S. Cl. .................. 324/158 P; 324/690; 324/687
[58] Field of Search .............. 439/42, 41; 324/686, 324/687, 688, 690, 158 P, 158 F

[56] References Cited

U.S. PATENT DOCUMENTS

| | | | |
|---|---|---|---|
| 2,954,521 | 9/1960 | McKee | 324/158 P |
| 3,400,331 | 9/1968 | Harris | 324/687 |
| 3,590,377 | 6/1971 | Sorger | 324/158 F |
| 3,771,051 | 11/1973 | Abbe | 324/688 |
| 3,803,489 | 4/1974 | Miller | 324/158 P |
| 4,477,774 | 10/1984 | Revirieux | 324/158 P |
| 4,801,866 | 1/1989 | Wixley | 324/158 P |
| 4,947,131 | 8/1990 | Mayer | 324/687 |

OTHER PUBLICATIONS

"The Measurement of Inhomogenities and of the Permittivity Disbribution in Mic–Substrates", Moschuering et al., IEEE Instrumentation and Measurement Technology Conference, Apr. 27–29, 1987, pp. 154–159.

"In Vivo Dielectric Properties of Human Skin from 50 MHz to 2.0 GHz", Grant, et al., Physics in Medicine and Biology, 1988, vol. 33, No. 5, pp. 607–612.

"A Precision Method for Measuring the Complex Permittivity of Solid Tissue in the Frequency Domain Between 2 and 18 GHz", Steel et al., Journal of Physics E, vol. 17, No. 1, 1984, pp. 30–34.

"Low-Temperature Radio-Frequency Matching Device", Golik et al., Instruments & Experimental Techniques, vol. 30, No. 2, Part 2, Mar.–Apr., 1987.

Primary Examiner—Kenneth A. Wieder
Assistant Examiner—Jose M. Solis
Attorney, Agent, or Firm—Hayes, Soloway, Hennessey & Hage

[57] ABSTRACT

A device and method for the determination of the dielectric characteristics of a material sample. The device includes a probe (3) connected to a coaxial line (2) by a connector (30). The probe comprises a conductive tubular member (78) having a conductive rod (8) coaxial to the tubular member and centered on the latter. An annular member is made of a dielectric material is housed in the tubular member, and is integral with the rod. The annular member/rod assembly is slidably carried in the tubular part (7). A resistive force urges the probe in contact with the material sample (4) so that good contact is ensured with the material sample.

10 Claims, 4 Drawing Sheets

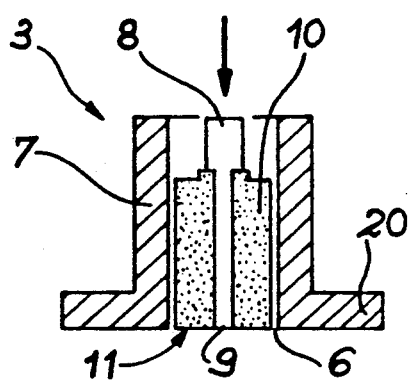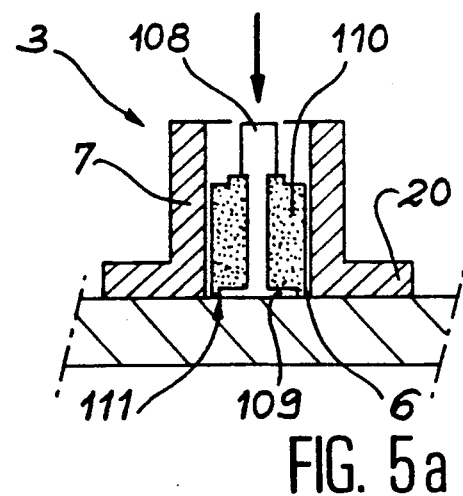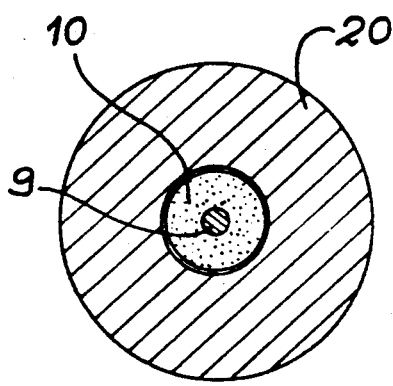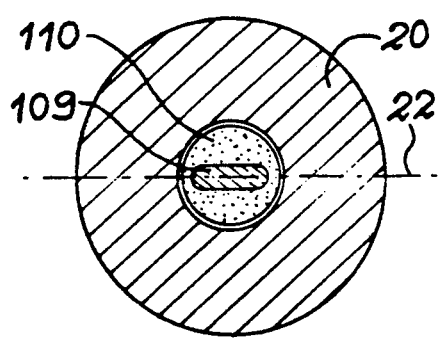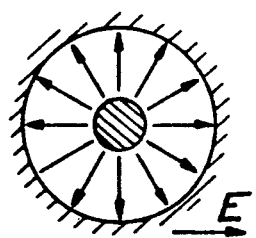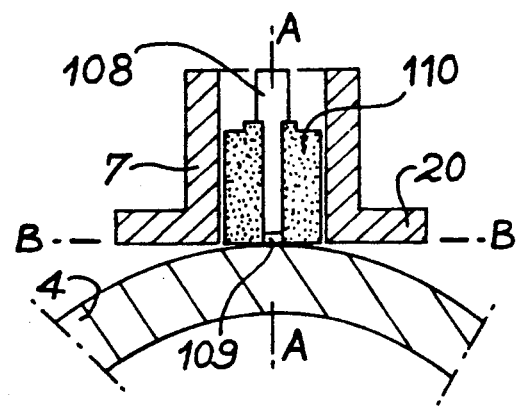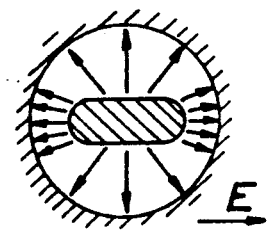

DEVICE FOR THE DIELECTRIC CHARACTERIZATION OF SAMPLES MADE OF A MATERIAL HAVING A FLAT OR UNEVEN SURFACE AND APPLICATION FOR THE NON-DESTRUCTIVE CONTROL OF THE DIELECTRIC HOMOGENEITY OF SAID SAMPLES

FIELD OF THE INVENTION

The present invention concerns devices for the dielectric characterization of samples made of a composite material having a flat or uneven shape. It is applicable for the non-destructive control of the surface homogeneity of these samples.

BACKGROUND OF THE INVENTION

The present invention more particularly concerns devices making it possible to determine the relative permittivity $\epsilon'$ and/or the losses $\epsilon''$ in the material in radiofrequency and hyperfrequency applications within a range from 100 MHz to 4 GHz.

The conventional techniques for the dielectric characterization of materials use coaxial lines, circular or rectangular guides and cavities. In most cases, these methods have the drawback of being destructive and it is essential to machine a sample with the shape of the measuring guide so as to place this sample inside the guide when carrying out measurements.

In this respect, reference may be made to the French patent application published under the No 2 619 223 and entitled "Method and device to assess the electromagnetic characteristics of a dielectric or magnetic material".

However, there are non-destructive measuring methods making use of cavities or open-ended coaxial lines. Some of these methods are referred to subsequently so as to clearly show the limits of the existing methods and illustrate the technical problems needing to be resolved.

When a closed cavity is used to carry out such measurements, this is limited by the range of frequencies.

In effect, the closed cavities in hyperfrequency applications are thus only applicable to small samples, usually those having dimensions less than 5×5 mm2. Reference may be made in this respect to the article by X. LE CLEAC'H which appeared in the journal Phys. Appl. 17 (1982), pp 481–490.

When a cavity is used, constituted by a "microstrip" line loop, it is possible to determine the electric conductivity $\alpha$ or the mobility $\mu$ in a semi conductive material. One embodiment was described by X. LE CLEAC'H, P-N FAVENNEC in the French patent application published under the No 2 623 291. Here again, the frequency is limited as the cavities have the drawback of being monofrequencies and the principle is based on a resonance technique.

As regards open-ended coaxial lines, the limitation concerns the nature of the materials to be controlled. In fact, open-ended coaxial lines have been examined as regards the measurement of the complex permittivity of biological substances in medical research applications and also of liquids and soft materials. In this respect, reference may be made to the article by STUCHLY and entitled "Equivalent circuit of an open-ended coaxial line in a lossy dielectric", IEEE Trans. Instrum. Meas. vol. IM-31, No 2, June 1982.

This limitation also exists for those methods generally using the coaxial probe technique. These probes can be used in a wide frequency band (100 MHz–4 GHz), but require good contact at the material/probe interface. This condition is only satisfied as regards the above-mentioned examples for liquids or soft materials, but remains a delicate unresolved point for "hard" materials.

SUMMARY OF THE INVENTION

The object of the invention is to provide a dielectric characterization device making it possible to overcome all these drawbacks.

In effect, the device of the invention makes it possible to accurately know the dielectric characteristics of samples made of a rigid composite material having an even or uneven shape with a known geometry in hyperfrequency and radiofrequency applications.

This device is also applicable to the non-destructive control of the dielectric homogeneity of such samples.

More specifically, the object of the invention is to provide a device for the dielectric characterization of samples made of a material having an even and/or uneven surface and including a probe connected to a coaxial line by a connector and mainly characterized in that the probe comprises:

a conductive tubular part, one of its extremities being intended to be connected to the external conductor of the connector, the other extremity forming the base of the probe extending outwardly so as to exhibit a flat ring-shaped surface, a conductive rod coaxial to the tubular part and centered in the latter and with one extremity intended to be in electric contact with the central conductor of the connector, a ring-shaped part made of a dielectric material housed in the tubular part rendered integral with the rod, its outer periphery being in friction contact with the internal surface of the tubular part, and characterized in that the rod/ring-shaped part unit slides by opposing a resistance when its second extremity is in contact with the sample, which ensures good contact with the latter, and characterized in that with this extremity having at least one axis which coincides with the generator of this surface, contact still takes place, irrespective of whether the surface is even or uneven.

So as to resolve the problem of contact between the probe and a sample made of a rigid material with a flat surface, the second extremity of the conductive rod has a circular shape so that the lines of the electric field $\vec{E}$, created when the probe is passed through by the currents transmitted by the coaxial line, are uniformly distributed around this rod.

So as to resolve the problem of contact between the probe and a flat or convex-surfaced sample made of a rigid material, the second extremity of the conductive rod has an elongated shape so as to favor the field lines on the outer edges approximately parallel to the longitudinal axis of this extremity.

According to one aspect of the invention, the conductive rod/annular part unit is rendered sliding and opposes a resistance by mechanical means.

According to another aspect of the invention, the conductive rod/annular part unit is rendered sliding and opposes a resistance by pneumatic and mechanical means.

According to one embodiment, at least one air intake is provided in the wall of the outer conductor upstream or downstream of the connection of the device with the coaxial line, and the extremities of the central conductor of the connector and conductive rod intended to be in contact have a shape adapted in such a way so that one of them is able to slide into the other.

The invention further concerns the non-destructive control of the dielectric homogeneity of material samples, this control being effected with the aid of a device as described previously, this control moreover consisting, if the sample is a flat sample, of placing the sample on a plate coupled to displacement means enabling the sample to be moved along two orthogonal axes (X, Y) within the plane of this plate, the device also being coupled to these displacement means which enable it to be moved above the plate along an axis (Z) orthogonal to the other two axes and wherein it consists of placing a sucker around the extremities of the seat of the probe of the device and of connecting this sucker to a vacuum pump so as to improve cladding of the device onto the sample at each measuring position. The uneven surface samples are placed on a rotating chuck.

BRIEF DESCRIPTION OF THE DRAWINGS

The invention shall be more readily understood from a reading of the following description, given by way of example and being in no way restrictive, with reference to the accompanying figures in which:

FIG. 4a represents the diagram of one section of the probe conforming to the invention along the axis AA of FIG. 3 and according to a first embodiment, FIG. 4b represents the diagram of a transversal section of the probe according to FIG. 4a with details of the distribution of the electric field lines on FIG. 4c, FIG. 5a represents the diagram of one section of the probe conforming to the invention along the axis AA of FIG. 3 according to a second embodiment, FIG. 5b represents the diagram of a transversal section of the probe according to FIG. 5a with details of the distribution of the electric field lines on FIG. 5d, FIG. 5c represents the diagram of one section of the probe placed on a sample with an uneven surface.

DETAILED DESCRIPTION OF THE PREFERRED EMBODIMENTS

The principle of the invention uses the basic open circuit coaxial line theory, as given in detail subsequently, in order to resolve the problem of contact (probe/material interface to be measured) on an even or uneven rigid dielectric.

The open circuit coaxial line is used as a probe or detector for the measurement of the dielectric characteristics of materials in radiofrequency and hyperfrequency applications.

Figure 1A:
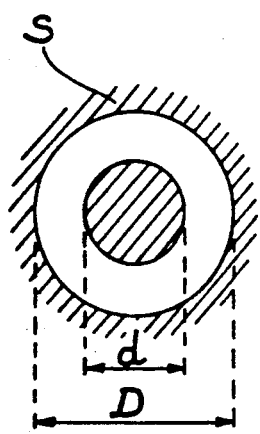
FIGS. 1a, 1b and 1c respectively represent the transversal and longitudinal sections and the equivalent electric circuit diagram of a coaxial line.
Figure 1B:
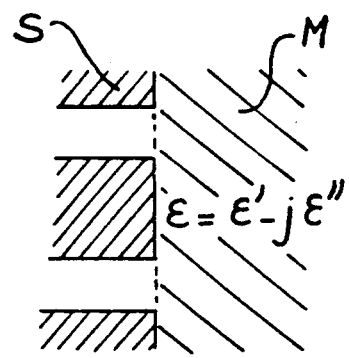
Figure 1C:
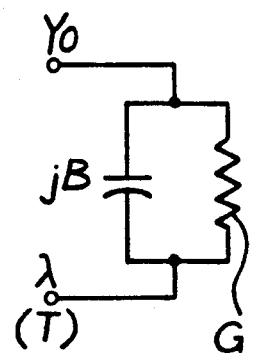

The principle of the method is based on measuring the reflection coefficient at the probe S/material M interface. The propagation of the line is effected according to the TEM mode and the elements are localized. The probe S is then represented by the equivalent circuit diagram of FIGS. 1a, 1b and 1c.

The reflection coefficient is directly linked to the admittance $Y = G + jB$, the impedance characteristic of the line being $Zo = 1/Yo$. The relative permittivity $\epsilon'$ is linked to the admittance by the following equation, namely $B = Co\omega\epsilon' + Cf\omega$, where $\omega = 2\pi F$, F being the frequency, Co the capacity linked to the electric field concentrated in the material in contact with the probe, and Cf the capacity linked to the electric field concentrated in the line. The conductance G is linked to the dielectric losses in the material.

Dielectric characterization consists of determining the permittivity $\epsilon'$ and the losses in the material $\epsilon''$ by using the following equations:

$$\epsilon' = \frac{B}{\omega \cdot Co} - \frac{Cf}{Co} = K'$$

$$\epsilon'' = \frac{G}{\omega \cdot Co} = K''$$

For frequencies exceeding 1 Ghz and for materials with high permittivity ($\epsilon' > 20$), it is necessary to take into account a term linked to the conductance Go of the probe opened in a free space, which is added to the preceding expressions:

$$\epsilon' = K' - \frac{Go}{\omega \cdot Co} \beta$$

with $\alpha + jB = (K' - jK'') 5/2$ $$\epsilon'' = K'' - \frac{Go}{\omega \cdot Co}$$

The quantities Co and Cf may be determined by calibration with the aid of known permittivity plates according to the frequency.

Figure 2:
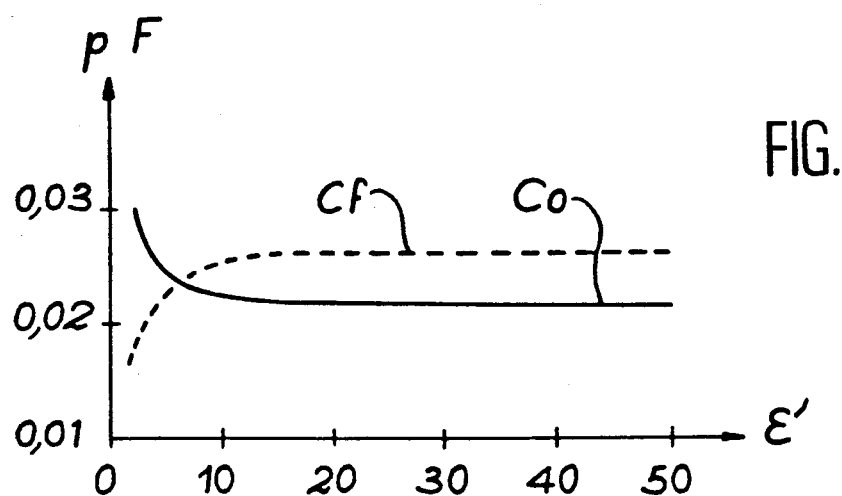
FIG. 2 represents the evolution of the capacities Co and Cf according to the permittivity $\epsilon'$ for a given frequency.

FIG. 2 shows the evolution of these capacities according to $\epsilon'$ at the frequency 1 GHz (calibration example of the probe determined experimentally in the case of the KMR standard).

Figure 3:
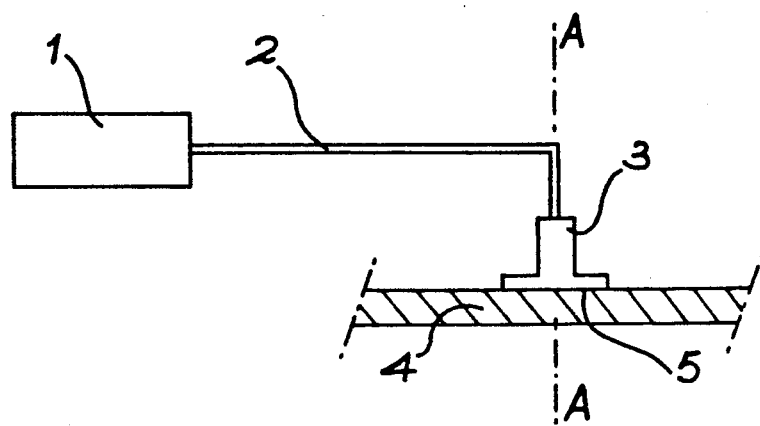
FIG. 3 represents a skeleton diagram of a device allowing for the dielectric characterization of rigid samples.

FIG. 3 is the skeleton diagram of a device allowing for the dielectric characterization of rigid samples in accordance with the invention.

This device comprises a measuring probe 3 connected by means of a coaxial line 2 to a vectorial network analyzer 1 (for example, an HP 8510B analyzer) which measures the impedance at the probe 3/material 4 interface 5 within the desired frequency band according to a particular embodiment (100 MHz–4GHz). The measurements are made in the entire frequency band by the same probe.

Figure 6:
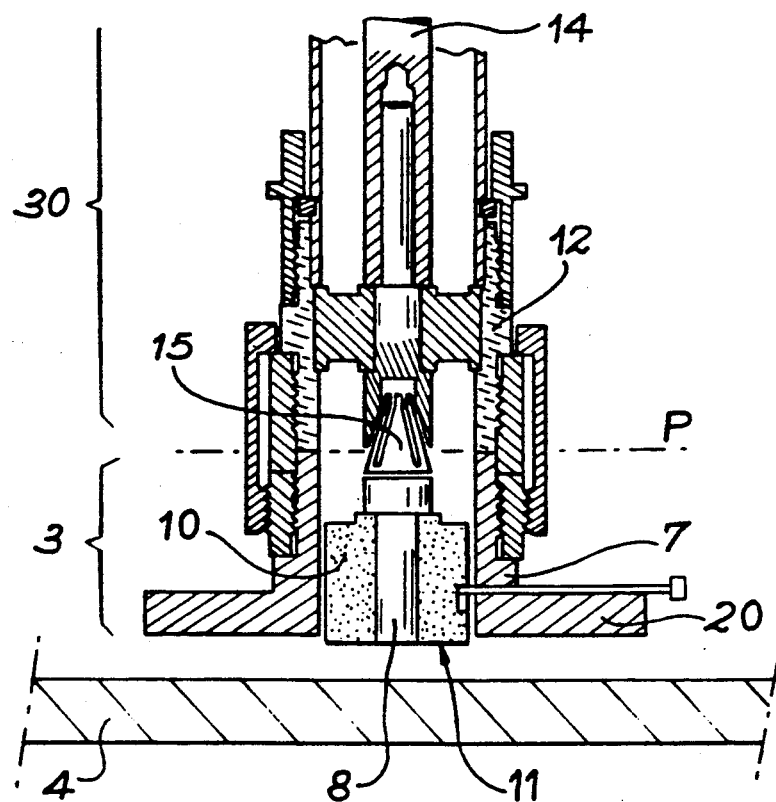
FIG. 6 represents a diagram of a more detailed section of the connector and a probe according to one embodiment variant.
Figure 7:
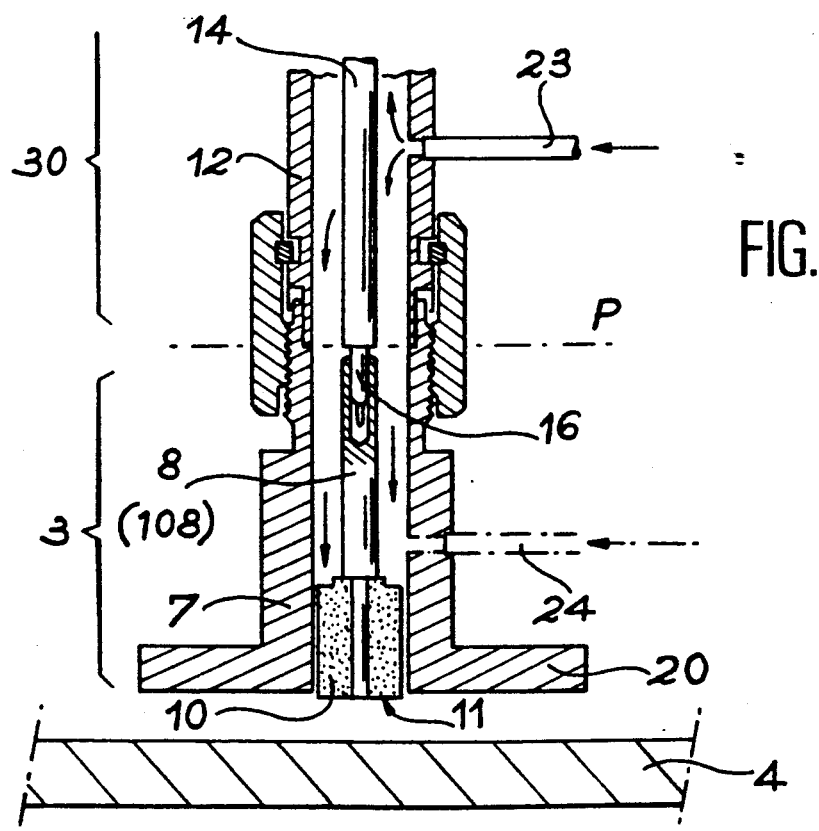
FIG. 7 represents a diagram of a more detailed section of the connector and a probe according to a second embodiment variant.

As can be seen on FIGS. 4a and 5a, the probe 3 is composed of:

an external conductive tubular part 7 whose upper extremity, as shown on the figure, is intended to be connected to the external conductor of the coaxial line by means of a connector 30 visible on FIGS. 6 and 7. The lower extremity 20 shown on the figure and forming the seating of the probe extends outwardly and exhibits a flat ring-shaped surface sufficiently large so as to ensure a good radiation of the probe (three times the internal diameter of the external conductor is selected, for example), a central section 11 (unit 8, 10), 111 (unit 108, 109, 110) composed of a conductive rod 8 or 108 coaxial to the tubular part 7 encompassed by an annular part 10 or 110 made of a dielectric material providing a sliding contact 6 with the external conductor 7.

On the figure, the upper extremity of the rod 8 or 108 is intended to be connected by means of a connector to the core of the coaxial line. The lower extremity is intended to be in contact with the material to be characterized.

The dielectric part 10 or 110 is integral with the rod 8 or 108.

As this shall be specified concerning FIGS. 6 and 7, the central section 11 is sliding and when moving, as indicated by an arrow, forces the dielectric part 10 (or 110) and the rod 8 (or 108) outside the tubular part.

FIG. 4b corresponds to a transversal section of the probe shown on FIG. 4a and shows an embodiment of the rod 8 in the case where the probe 3 is intended to carry out measurements on flat-surfaced samples.

The shape of the rod is circular so that the lines of the electric field $\vec{E}$, created when the probe is passed through by currents transmitted by the coaxial line, are distributed uniformly around this rod (as shown in detail on this figure).

FIGS. 5a, 5b and 5c correspond to the embodiment of a probe for carrying out measurements on samples having an uneven surface (or convex in the example described).

The extremity 109 of the rod 108 has an elongated shape so as to favor the field lines on the outer edges which are approximately parallel to the longitudinal axis 22 of this extremity.

The section of the probe of FIG. 5a is taken in a plane passing through the longitudinal axis of the extremity 109 existing along a generator of the material 4.

The section shown on FIG. 5c shows the convex shape of the material 4.

In the case of uneven shapes (FIG. 5c), the volume of air between the material and the probe is a source of error concerning the determination of the dielectric characteristics. So as to minimize (or even eliminate) this error, a correction factor is used in the calculation making it possible to go back to the complex permittivity values of the material.

This correction factor is deduced conventionally on the basis of a calibration with the aid of materials with known characteristics and shapes and makes it possible to link the measured equivalent value in the presence of the volume of air with the real value of the material.

FIGS. 6 and 7 represent the more detailed diagram of a probe 3 connected to a connector 30 viewed along a longitudinal section. The plane P is the probe/connector interface plane.

FIG. 6 corresponds to a first embodiment variant (corresponding to the standard APC7) making it possible to obtain a central sliding section 11 or 111 which opposes a resistance when it is in contact with the material. The central section 11 (or 111) is rendered sliding according to this first variant by mechanical means (mechanical thrust). These mechanical means are embodied by a movable and removable conductive part 15 whose lower extremity on the figure is cladded against the upper extremity of the conductive rod. The upper extremity of this part 15 has the shape of a funnel adapted to partly penetrate inside the extreme section of the core 14 placed in the connector and at the same time providing an electric contact.

This part 15 thus ensures electric continuity between the central conductor 14 of the connector 12 and the central conductor 8 (or 108). When the probe 3 is connected to the connector 30, the part 15 pushes back the internal body 11 sliding in the outer conductor 7 of the probe. The moment the probe is cladded against the material 4, the internal body 11 shall push back the part 15 into its central conductor 14. Thus, the rod 8 of the probe shall always be in contact with firstly the central conductor 14 of the connector and secondly with the material to be tested.

FIG. 7 shows a second embodiment variant corresponding to the KMR standard. This second variant makes it possible to obtain a central section 11 (or 111) sliding by mechanical or pneumatic means, the thrust being pneumatic. One compressed air intake is provided, either in the connector 30 or in the probe 3. For the purpose of simplification, both the possible solutions are shown on FIG. 7.

The extremity of the central conductor 16 is fixed. So as to ensure movement of the part 11 of the probe 3, compressed air is sent by excess pressure into the connector 30 by the intake 23 or into the probe 3 by the intake 24 and has the effect of pushing back the part 11 (spring effect).

It is only when the probe is in contact with the material that the part 11 of the probe comes into contact with the central conductor 14 via its extremity and accordingly the measurement is able to be carried out.

Figure 8:
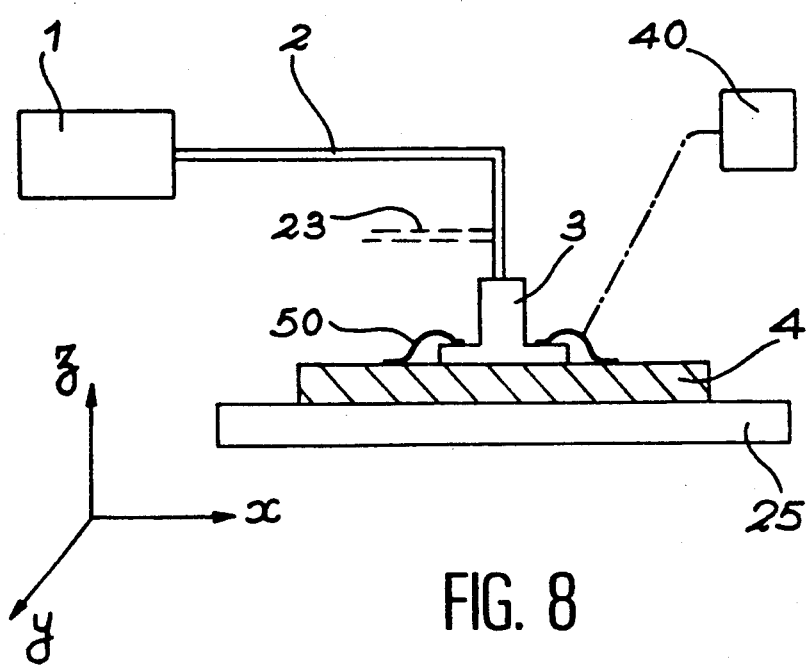
FIG. 8 represents the diagram of the device for controlling the dielectric homogeneity of a sample conforming to the invention.

FIG. 8 shows an example of a device for the non-destructive control of the local dielectric characteristics of a sample and the dielectric homogeneity of this sample.

The sample 4 is secured to a plate 25 moved by displacement means along two axes X or Y with conventional crossed movements (not shown). These means also make it possible to have a movement along the direction Z so as to bring the probe into mechanical contact with the sample. A conventional vacuum pump 40, connected to a sucker 50 placed around the device, makes it possible to obtain good material/probe contact. The plate 25 then makes it possible to move the sample along the directions X and Y when the probe is spaced from the sample so as to enable a measurement to be carried out at a new point. The movements required and the measurements are effected automatically by means of a computer and a digital program which also restores the dielectric characteristics of the material. Any conventional device with digital control makes it possible for an expert in this field to easily control movements of the plate and obtain the desired calculations.

Figure 9:
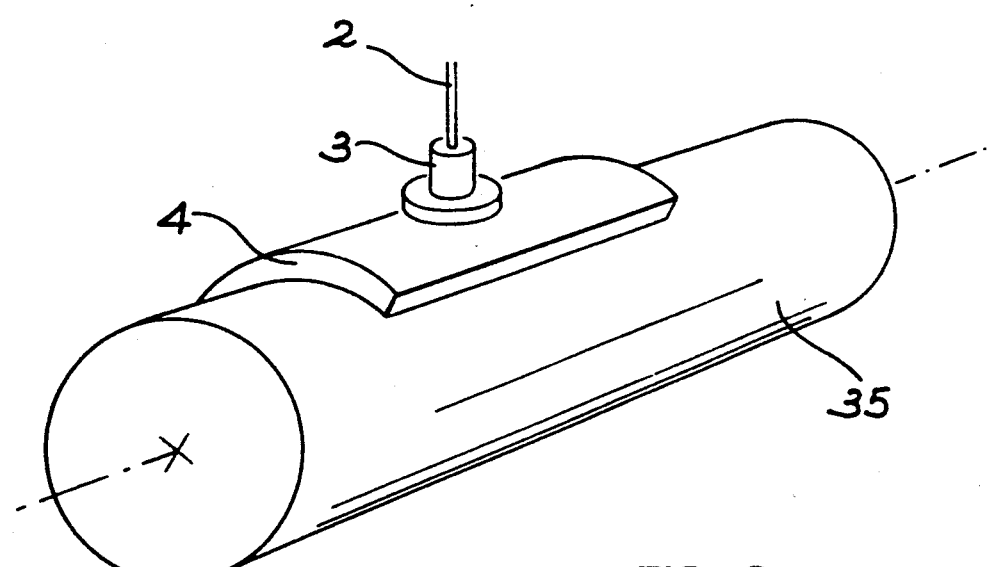
FIG. 9 represents one embodiment variant adapted to the control of samples having an uneven surface.

As shown on FIG. 9, so as to control cylindrical or conical, shapes, the measurement principle is the same, but the displacement mechanism differs in that the sample is placed on a rotating chuck 35 provided with a displacement along the axis Z. The device makes it possible to scan all the generators of the cylindrical or conical sample.

By way of example, two devices have been made available on the basis of APC7 and KMR standard probe models. The principle of the invention may clearly be applied to other standards, such as the GR900 (larger model) or K (smaller model) standards.

What is claimed is:

1. A device for measuring the dielectric characteristics of material samples by contacting the surface of the samples, said device including a probe connected to a coaxial line by a connector, wherein the probe comprises:

a conductive tubular member having one end connected to the outer conductor of the connector and the other end forming the base of the probe extending outwardly so as to provide a flat annular surface, a conductive rod coaxial to the tubular member and centered on the latter and having one end in electrical contact with the central conductor of the connector, an annular member made of a dielectric material and integral with the rod, slidably carried within the tubular member with the annular member's outer periphery in frictional contact with the inner surface of the tubular member, and resistive force means operating on the annular member/rod assembly whereby to urge the other end of the conductive rod in contact with the sample to be measured, thus ensuring good contact with the sample.

2. A device according to claim 1, wherein the other end of the conductive rod has a circular shape such that the electric field lines, generated by the transmission of electric currents through the probe after having passed through the coaxial line, are distributed uniformly around the rod.

3. A device according to claim 1, wherein the other extremity of the conductive rod has an elongated shape such that the electric field lines generated on the outer edges of the end of the rod opposite the said one end are oriented approximately parallel to the longitudinal axis of the rod said opposite end.

4. A device according to claim 1, wherein the resistive force means comprises a mechanical force means.

5. A device according to claim 1, wherein the resistive force means comprises pneumatic force means.

6. A device according to claim 5, and including at least one air intake in the wall of the outer conductor upstream of the connection of the probe to the coaxial line, for directing pressured air on the probe.

7. A device according to claim 5, and including at least one air intake in the wall of the outer conductor downstream of the connection of the probe to the coaxial line, for directing pressured air on the probe.

8. A device according to claim 5, wherein the mating ends of the central conductor of the connector and the conductive rod are shaped so that one is slidable into the other.

9. A method for measuring the dielectric characteristics of a material sample by means of a measuring probe in contact with the surface, comprising the steps of:

(a) placing the material sample onto a plate which is coupled to means for displacing said plate along two orthogonal axes within the plane containing said plate;

(b) coupling said material sample to an orthogonal displacement means for displacing said material sample along an axis orthogonal to the plane containing said plate;

(c) connecting a vacuum pump to a suction device positioned around the lower portions of the measuring probe in contact with a first measuring point on the surface of said material sample, such that a substantially air-tight seal is formed between the surface of said material sample and the lower portions of the probe;

(d) creating suction between the surface of said material sample and the probe such that good contact is maintained between the surface of said material sample and said probe at said first measuring point;

(e) conducting a measurement at said first measuring point;

(f) moving said probe to a new measuring point;

(g) creating suction between the surface of said material sample and the probe such that good contact is maintained between the surface of said material sample and said probe at said new measuring point;

(h) conducting a measurement at said new measuring point; and (i) repeating steps (f) to (h) in sequence.

10. A method for measuring the dielectric characteristics of a material sample by means of a measuring probe in contact with the surface of the sample, wherein the sample has a curved shape, comprising:

(a) removably fixing the sample onto a chuck, said chuck having rotation means allowing said chuck to rotate about an axis different from the axis of the probe, said chuck also having displacement means allowing said chuck to be displaced along an axis parallel to the axis of the probe;

(b) connecting a vacuum pump to a suction device positioned around the lower portions of the measuring probe in contact with a first measuring point on the surface of said material sample, such that a substantially air-tight seal is formed between the surface of said material sample and the lower portions of the probe;

(c) creating suction between the surface of said material sample and the probe such that good conduct is maintained between the surface of said material sample and said probe at said first measuring point;

(d) conducting a measurement at said first measuring point;

(e) moving said probe to a new measuring point;

(f) creating suction between the surface of said material sample and the probe such that good contact is maintained between the surface of said material sample and said probe at said new measuring point;

(g) conducting a measurement at said new measuring point; and (h) repeating steps (f) to (h) in sequence.

* * * * *